(12) United States Patent
Vogt et al.

(10) Patent No.: US 7,358,232 B2  
(45) Date of Patent: *Apr. 15, 2008

(54) METHOD FOR THE ANTIBIOTIC COATING OF BODIES WITH INTERCONNECTING MICROCAVITIES AS WELL AS COATED BODIES AND THEIR USAGE

(75) Inventors: Sebastian Vogt, Jena (DE); Matthias Schnabelrauch, Jena (DE); Klaus-Dieter Kühn, Marburg (DE)

(73) Assignee: Heraeus Kulzer GmbH & Co.KG, Hanau (DE)

( * ) Notice: Subject to any disclaimer, the term of this patent is extended or adjusted under 35 U.S.C. 154(b) by 60 days.

This patent is subject to a terminal disclaimer.

(21) Appl. No.: 10/174,682

(22) Filed: Jun. 19, 2002

(65) Prior Publication Data

US 2003/0049324 A1  Mar. 13, 2003

(30) Foreign Application Priority Data

Aug. 31, 2001  (DE) ............................... 101 42 464  
Feb. 1, 2002   (DE) ............................... 102 04 308

(51) Int. Cl.
*A61K 31/70* (2006.01)
*C07H 15/02* (2006.01)

(52) U.S. Cl. .................. 514/25; 424/422; 514/27; 514/28; 514/29; 536/16.8; 623/1.11

(58) Field of Classification Search .............. 424/423  
See application file for complete search history.

(56) References Cited

U.S. PATENT DOCUMENTS

| | | | |
|---|---|---|---|
| 3,091,572 A | | 5/1963 | Luedemann et al. |
| 4,291,013 A | | 9/1981 | Wahlig et al. ............... 424/16 |
| 4,322,398 A | * | 3/1982 | Reiner et al. ............... 424/425 |
| 4,617,293 A | | 10/1986 | Wahlig et al. ............... 514/41 |
| 4,879,135 A | * | 11/1989 | Greco et al. ............... 326/1.48 |
| 5,019,096 A | * | 5/1991 | Fox et al. ............... 600/36 |
| 5,679,646 A | * | 10/1997 | Cimbollek et al. ........... 514/43 |

2002/0183265 A1  12/2002  Vogt et al. ............... 514/29

FOREIGN PATENT DOCUMENTS

| | | |
|---|---|---|
| DE | 2 301 633 | 11/1973 |
| DE | DT 2 301 633 | 11/1973 |
| DE | DT 24 46 640 A1 | 12/1975 |
| DE | 28 07 132 A1 | 8/1979 |
| DE | 32 48 328 A1 | 6/1984 |
| DE | 101 14 245 A1 | 10/2002 |
| EP | 0 087 662 | 9/1983 |
| GB | 1 400 464 | 7/1975 |
| NL | 6609490 | 7/1966 |
| WO | 94 08599 | 4/1994 |
| WO | 97 38698 | 10/1997 |

OTHER PUBLICATIONS

Abstract—Folch Vazquez, Conrado; "Tetracycline lauryl sulfate"; Span., 7 pp.  
Cimbollek, Monika, et al.; U.S. 5,679,646-"Solvent for a Sparingly Soluble Gentamicin Salt"; Oct. 21, 1997 abst. only.

* cited by examiner

*Primary Examiner*—Michael G. Hartley  
*Assistant Examiner*—Nabila G Ebrahim  
(74) *Attorney, Agent, or Firm*—Norris McLaughlin & Marcus PA

(57) ABSTRACT

The invention relates to a method for the antibiotic coating of bodies with interconnecting microcavities as well as bodies coated this way and their usage. The invented method is characterized in that in the microcavities of non-metallic bodies an aqueous solution 1, which contains at least one easily water-soluble antibiotic component from the groups of the aminoglycoside antibiotics, the tetracycline antibiotics, the lincosamide antibiotics and the 4-quinolone antibiotics, and an aqueous solution 2, which contains at least one easily water-soluble amphiphilic component from the groups of the alkyl sulfates, alkyl sulfonates, alkylaryl sulfates, dialkylaryl sulfates, alkylaryl sulfonates, dialkylaryl sulfonates, cycloalkyl sulfates, cycloalkyl sulfonates, alkylcycloalkyl sulfates, are introduced, wherein between the introduction of solutions 1 and 2 the water is basically removed through vaporization and/or evaporation, and whereby from the components of solutions 1 and 2 in the microcavities a deposit is formed, which is sparingly soluble in water.

24 Claims, No Drawings

METHOD FOR THE ANTIBIOTIC COATING OF BODIES WITH INTERCONNECTING MICROCAVITIES AS WELL AS COATED BODIES AND THEIR USAGE

The present invention relates to a method for the antibiotic coating of bodies with interconnecting microcavities through treatment with a 2-component system as well as such a body and its usage.

Bone defects occur relatively frequently in human and veterinary medicine and are caused in particular through bone fistulas, comminuted fractures and tumors. In the case of open comminuted fractures, frequently additional infections of the bone tissue are observed. The treatment of bone defects can occur through a filling process with suitable implants. Over the last few years, in particular porous implants, which due to their chemical composition and their porous structure have an osteo-conductive effect and favor a growing in with the surrounding bone tissue, have gained interest. The treatment of bone defects becomes problematic whenever additional microbial infections of the bone tissue exists. Infections of the bone tissue can be counteracted through the systemic or local application of suitable antibiotics. The systemic application of antibiotics is problematic due to the in part not inconsiderable toxicity of the antibiotics. The local application directly in or on the infected tissue on the other hand offers the advantage that high local antibiotics concentrations can be achieved while avoiding damaging antibiotics concentrations in the remaining organism. These high local antibiotics concentrations at the location of the bacterial infections allow the microorganisms to be killed almost completely so that the bacterial infections can be treated very efficiently. It is particularly advantageous if at the location of the bacterial infection an effective antibiotic concentration is maintained over the course of several days to weeks so as to allow the antibiotic to penetrate into the infected tissue as deeply as possible and thus destroy even germs that are difficult to access. Soft tissue defects with bacterial infections can also be found frequently in human and veterinary medicine. Local antibiotics treatment is therefore also of interest for the treatment of these types of infections.

Until now, sparingly soluble salts of the aminoglycoside antibiotics, the tetracycline antibiotics and the lincosamide antibiotics met with relatively little interest in the production of controlled-release drugs and of antibiotically effective implants. The synthesis of sparingly soluble salts or chelates of the antibiotics of the tetracycline type has been general knowledge for decades. Folch Vazquez for example describes the production of tetracycline dodecyl sulfate through the conversion of tetracycline hydrochloride with sodium dodecyl sulfate in water (C. Folch-Vazquez: Tetracycline lauryl sulfate. Feb. 8, 1966, ES 3309402; C. Folch Vazquez: Tetracycline derivatives. Jan. 9, 1967, NL 6609490).

Among the aminoglycoside antibiotics, a series of sparingly soluble salts is also basically known. Hence, for gentamicin, the presentation of sparingly soluble salts based on higher fatty acids, arylalkyl carboxylic acids, alkyl sulfates and alkyl sulfonates was described (G. M. Luedemann, M. J. Weinstein: Gentamycin and method of production. Jul. 16, 1962, U.S. Pat. No. 3,091,572). Examples of this are gentamycin salts of lauric acid, stearic acid, palmitic acid, oleic acid, phenyl butyric acid, and naphthalene-1-carboxylic acid. The synthesis of dodecyl sulfates of gentamycin in aqueous or aqueous-methanol solution is described by Jurado Soler et al. (A. Jurado Soler, J. A. Ortiz Hernandez, C. Ciuro Bertran: New gentamycin derivatives, method for production of same and antibiotically effective composition containing it. Sep. 30, 1974, DE 24 46 640). These salts, however, often proved to be unfavorable because they represent wax-like, hydrophobic substances, which impair a galenic usage. Furthermore fatty acid salts and aliphatic sulfates of gentamycin and of etamycin were synthesized from the free base or its salts in water at 50-80° C. (H. Voege, P. Stadler, H. J. Zeiler, S. Samaan, K. G. Metzger: Sparingly soluble salts of aminoglycosides as well as formulations containing them with delayed active substance release. Dec. 28, 1982, DE 32 48 328). These antibiotics fatty acid salts are said to be suited as injection drugs. Sparingly soluble aminoglycoside flavonoid phosphates represent a more recent development (H. Wahlig, E. Dingeldein, R. Kirchlechner, D. Orth, W. Rogalski: Flavonoid phosphate salts of aminoglycoside antibiotics. Oct. 13, 1986, U.S. Pat. No. 4,617,293). The salts of phosphoric acid mono-esters of derivatives of hydroxy flavanes, hydroxy flavenes, hydroxy flavanones, hydroxy flavones and hydroxy flavylium are described. Particularly preferred are the derivatives of the flavanones and flavones. These sparingly soluble salts are supposed to be used as controlled-release drugs. For example, these salts are introduced into collagen shaped masses (H. Wahlig, E. Dingeldein, D. Braun: Medicinally useful, shaped mass of collagen resorbable in the body. Sep. 22, 1981, U.S. Pat. No. 4,291,013). Furthermore, artificial heart valves were also impregnated with these sparingly soluble gentamycin salts, Gentamicin Crobefat (M. Cimbollek, B. Nies, R. Wenz, J. Kreuter: Antibiotic-impregnated heart valve sewing rings for treatment and prophylaxis of bacterial endocarditis. Antimicrob. Agents Chemother. 40(6) (1996) 1432-1437).

The production of simple controlled-released antibiotic(s) drugs in the pore systems of porous bodies through the impregnation of porous bodies with aqueous antibiotics solutions is general knowledge (R. Reiner, W. Kiβing, H. Döring, K. Köster, H. Heide: Implantable controlled-release pharmaceutics drug. Feb. 20, 1978, DE 28 07 132). Here a retarding active ingredient release of the in water soluble active ingredient can be accomplished through adsorption and/or through diffusion processes, which depends on the material that is used, the pore volume and porosity.

Apart from that, it is also possible to dissolve sparingly water-soluble antibiotics salts in suitable organic solvents and impregnate the molded bodies with these solutions. This creates deposits of active ingredients in the molded bodies, which have a retarding active ingredient release. One example is the method for dissolving a gentamicin salt sparingly soluble in water and its usage for coating purposes described by Cimbollek and Nies (M. Cimbollek, B. Nies: Solvent for a sparingly soluble gentamicin salt. May 4, 1994, U.S. Pat. No. 5,679,646). This gentamicin salt on the basis of 3-p-methoxy benzylidene-6-hydroxy-4'-methoxy flavanone-6-phosphate however must be synthesized before the coating process. Kurtz describes a very interesting variation, in which sparingly water-soluble antibiotics salts are formed in situ on an absorbing substrate such as bandage material through consecutive impregnation with a solution of an alkaline gentamicin salt or a polymycin salt and an acid penicillin or cephalosporin salt under precipitation (L. D. Kurtz: Water-insoluble biocide antibiotics salts. Nov. 13, 1973, DE 23 01 633). The penicillin or cephalosporin radicals form the anionic component of the salts, and the cationic aminoglucoside radicals form the cationic component.

This interesting concept was not addressed again later on and was also not checked for its suitability for other sparingly water-soluble salts of the aminoglycoside antibiotics, the tetracycline antibiotics, the lincosamide antibiotics and the 4-quinolone antibiotics. So far no similar impregnation methods for the production of antibiotics drugs in porous bodies while utilizing anionic radicals from the groups of organic sulfates and sulfonates are known.

The layer-forming properties of in water sparingly soluble antibiotics salts on the basis of organic sulfates and sulfonates also did not receive any attention so far.

In summary, it should be noted that so far no methods are known where antibiotic coatings are applied onto the surface of interconnecting pore systems, which consist of sparingly water-soluble salts of the aminoglycoside antibiotics, the tetracycline antibiotics, the lincosamide antibiotics and the 4-quinolone antibiotics, and which are synthesized directly in the microcavities proceeding from water-soluble antibiotics salts and water-soluble organic sulfates or sulfonates.

The present invention is based on the task of developing an uncomplicated, inexpensive method for the antibiotic coating of bodies with interconnecting microcavity systems. These antibiotically equipped interconnecting porous bodies should be used as implants in human and veterinary medicine for the treatment of bone defects and possibly for the treatment of soft tissue. In this connection, a continuous release of antibiotics from the antibiotic coating located on the interior surface of the interconnecting microcavities over a period of several days to several weeks is sought, so that a microbial infection in the area of the bone defect that is to be treated and/or soft tissue defect can be effectively prevented or counteracted.

One objective is to create antibiotic coatings which enable an antibiotics release over a period of several days in a simple manner while avoiding toxic solvents and while dispensing with polymer binders. Furthermore it is the object to make a suitable method available for several types of antibiotics. In doing so, it is beneficial if the antibiotic coating adheres well to the interior surface of bodies with interconnecting microcavities and there is no risk that the interconnecting microcavities can become clogged.

The task is resolved with the features of the independent claims. Beneficial embodiments result from the dependent claims.

The invention is based upon the surprising finding that antibiotic coatings with good adhesive properties and retarding active ingredient release are formed in the interconnecting microcavities by bodies if first an aqueous solution 1, which contains at least one easily water-soluble antibiotic component from the groups of the aminoglycoside antibiotics, the tetracycline antibiotics, the lincosamide antibiotics, the 4-quinolone antibiotics and the chlorhexidines, and subsequently, after evaporation and/or vaporization of the water, an aqueous solution 2, which contains at least one water-soluble amphiphilic component from the groups of the alkyl sulfates, the alkyl sulfonates, the alkylaryl sulfates, dialkylaryl sulfates, alkylaryl sulfonates, dialkylaryl sulfonates, cycloalkyl sulfates, cycloalkyl sulfonates, the alkylcycloalkyl sulfates are introduced in a suitable manner, e.g. through dipping, spraying or dripping.

Antibiotic coatings are also formed when first aqueous solution 2, and subsequently, after removal of the water, aqueous solution 1 is introduced into the micro hollow space spaces through dipping or spraying or dripping.

Interconnecting microcavities in this context mean that pores and also cavities of irregular shape are connected with each other through channels and do not exist separately like a closed-cell cellular material. Preferred materials are inorganic materials such as porous glass or porous ceramics.

According to the invention, in the interconnecting micro hollow space system, solid bodies synthesize a slightly water-soluble deposit of one or more antibiotic substances from the groups of the aminoglycoside antibiotics, the tetracycline antibiotics, the lincosamide antibiotics, the 4-quinolone antibiotics and the chlorhexidines and at least one water-soluble salt from the group of the alkyl sulfates, alkyl sulfonates, the alkylaryl sulfates, dialkylaryl sulfates, alkylaryl sulfonates, dialkylaryl sulfonates, the cycloalkyl sulfates, the cycloalkyl sulfonates, the alkylcycloalkyl sulfates and form antibiotic coatings. The antibiotic coatings created in the microcavities exhibit a delayed active ingredient release in an aqueous environment over a period of several days to weeks. In particular the antibiotics products of the alkyl sulfates and alkyl sulfonates precipitate from the aqueous solution during the synthesis in a flaky manner as wax-like, non-crystalline substances, which during the drying process exhibit a certain course and are deposited on surfaces as a coating. They adhere surprisingly well on glass, ceramics and polymer surfaces.

Usage of the alkyl sulfates, the alkyl sulfonates, the alkylaryl sulfates, dialkylaryl sulfonates, alkylaryl sulfonates, dialkylaryl sulfonates, the cycloalkyl sulfates, the cycloalkyl sulfonates and the alkylcycloalkyl sulfates in the acid form instead of the salt form also lies within the meaning of the invention.

The particular advantage of the method of the invention is that the sparingly water-soluble antibiotic deposits are created only under in situ conditions in the interconnecting microcavities and do not have to be previously synthesized separately. The method allows a very inexpensive, simple antibiotic coating of the interior surface of porous bodies of the most varied material compositions to be realized. The sparingly water-soluble deposits adhere to the pore surface and are mechanically protected in the microcavities. This way, an additional polymer binding agent for the mechanical stabilization of the coating can be dispensed with. Upon dissolving the slightly water-soluble deposits, therefore, no undesirable adjuvants remain in the microcavities. The method is suitable in particular also for the production of antibiotic coatings in micro-porous pore systems.

According to the invention, allomycin, amicetin, amikacin, apramycin, bekanamycin, betamicin, butirosin, destomycin, dibekacin, dihydrostreptomycin, flambamycin, fortimycin A, fortimycin B, framycetin, gentamicin, hikizimycin, homomycin, hybrimycin, hygromycin B, kanamycin, kasuhamycin, lividomycin, minosamino[m]ycin, neomycin, netilmicin, paromomycin, parvulomycin, puromycin A, ribostamycin, rimocidin, ristosamine, ristomycin, sagamycin, sisomicin, sorbistin, spectinomycin, streptomycin, tobramycin, tunicamycin, verdamycin from the group of the aminoglycoside antibiotics are preferred as antibiotic components in aqueous solution 1.

Clindamycin and lincomycin are preferred from the group of the lincosamide antibiotics as the antibiotic component in aqueous solution 1.

Tetracycline, chlortetracycline, oxytetracyline, demethylchlortetracycline, methacycline, doxycycline, rolitetracycline and minocycline are preferred from the group of the tetracycline antibiotics as antibiotic components in aqueous solution 1.

Ciprofloxacin, moxifloxacin and enfloxacin are preferred from the group of the 4-quinolone antibiotics as antibiotic components in aqueous solution 1.

From the group of the chlorhexidines chlorhexidine-dichloride, chlorhexidine-di-acetate and chlorhexidine-di-gluconate are preferred as antibiotic components in aqueous solution 1.

Aqueous solution 1 preferably contains 0.1 to 60 percent by mass of an easily water-soluble antibiotic component from the group of the aminoglucoside antibiotics, the lincosamide antibiotics, the tetracycline antibiotics, the 4-quinolone antibiotics and the chlorhexidines.

Aqueous solution 2 preferably contains 0.1 to 60 percent by mass of an in water soluble amphiphilic component from the groups of the alkyl sulfates, the alkyl sulfonates, the alkyl aryl sulfates, dialkylaryl sulfates, alkylaryl sulfonates, dialkylaryl sulfonates, the cycloalkyl sulfates, the cycloalkyl sulfonates, the alkylcycloalkyl sulfates.

The ratio of the substance quantity of the easily water-soluble antibiotic component of aqueous solution 1 to the substance quantity of the in water soluble amphiphilic component of aqueous solution 2 is appropriately 1:1 to 6:1.

In aqueous solution 1 the antibiotic component beneficially exists in the form of a protonized salt, whereby chloride ions, bromide ions, hydrogen sulfate ions, sulfate ions, dihydrogen phosphate ions, hydrogen phosphate ions, phosphate ions, acetate ions, succinate ions and lactate ions are preferred as counter-ions.

When introducing the aqueous solutions 1 and 2 into the microcavities, preferably the capillary effect should be taken advantage of, i.e. for example it can occur through complete or partial impregnation, through spraying, dripping or dropping.

In the case of gentamicin, appropriately initially an aqueous solution of for example gentamicin sulfate is introduced into the microcavities through dipping or spraying or dripping, followed by a drying process so as to remove the water from the pores, followed by an introduction of an aqueous solution of sodium dodecyl sulfate and/or an aqueous solution of sodium dodecyl sulfonate through dipping or spraying or dripping.

In the case of ciprofloxacin, initially an aqueous solution of ciprofloxacin hydrochloride is introduced into the pores through dipping or spraying or dripping, followed by a drying process so as to remove the water from the pores and a subsequent introduction of an aqueous solution of sodium dodecyl benzyl sulfonate through dipping or spraying or dripping.

In the case of tetracyclines, it is appropriate to introduce an aqueous solution of tetracycline hydrochloride and/or chlortetracycline hydrochloride and/or minocycline hydrochloride and/or doxycycline hydrochloride into the pores through dipping or spraying or dripping, followed by a drying process so as to remove the water from the pores, and a subsequent introduction of an aqueous solution of sodium dodecyl sulfate and/or an aqueous solution of sodium dodecyl sulfonate through dipping or spraying.

It is appropriate to remove the water basically completely after the first solution has been introduced. This can take place for example through a drying process in a flow of gas or through the application of a partial vacuum or also thermally. Freeze drying is also possible and could be beneficial with sensitive antibiotic active substances. The type of drying process (temperature and pressure) can also influence the structure of the antibiotic coating. The type of drying process can be adjusted to fibrous bodies with interconnecting micro hollow space systems, such as shaped masses, felt or fabrics.

After introducing the first aqueous solution into the pores, the water can be removed again, either partially or completely, at normal pressure or in a vacuum at temperatures of −20° C. to 120° C.

After the slightly water-soluble deposits have formed, the molded bodies can be dried at normal pressure or in a vacuum at temperatures of −20° C. to 120° C. A vacuum here should be interpreted as the conventional negative pressure, which is generally applied so as to remove water.

Sodium dodecyl sulfate, sodium dodecyl sulfonate, sodium tetradecyl sulfate, sodium tetradodecyl sulfonate, sodium hexadecyl sulfate, sodium hexadecyl sulfonate, sodium octadecyl sulfate, sodium octadecyl sulfonate and sodium dodecyl benzyl sulfonate have proven particularly useful as water-soluble amphiphilic components of aqueous solution 2.

The bodies with interconnecting microcavities can be made up of inorganic or organic or polymer organic materials, or represent inorganic-organic composite materials.

In the first case they preferably consist of hydroxyl apatite, tricalcium phosphate, calcium carbonate, calcium sulfate, resorbable glass, resorbable glass ceramics or combinations of these materials.

In the second case they are made up of e.g. polymers, such as on the basis of L-lactic acid and/or D-lactic acid and/or glycolic acid and/or 2-hydroxyethyl-oxy acetic acid. Such polymer systems are available for example under the brand name Resomer® from Boehringer Ingelheim.

The bodies with interconnecting microcavities can also be formed from metal or metal alloys, in particular titanium, titanium alloys or stainless steel. Metallic bodies with interconnecting microcavities should be interpreted as such metallic bodies, which on their surface contain microcavities that are connected with one another, and they also include metallic bodies whose surface has been roughened through sand-blasting in such a way that they contain open cavities that are connected with each other in the metal surface.

According to the invention, it is also possible that the bodies with interconnecting microcavities take on the shape of shaped masses, felt, fabric and knits.

Additionally it is possible according to the invention that the antibiotic coatings do not completely fill in the volume of the interconnecting microcavities of the solid bodies.

It can prove beneficial to add solvents that can be mixed with water, such as methanol, ethanol, isopropanol, N,N-dimethyl formamide and/or dimethyl sulfoxide as co-solvents to the aqueous solution 1 or 2 so as to increase solubility.

It is in accordance with the invention to use the antibiotically coated, interconnecting porous bodies as implants.

It is also within the meaning of the invention to introduce solution 2 into the bodies with interconnecting micro cavity systems, and after removal of the water to use bodies treated this way with interconnecting micro hollow space systems as implant materials, into which solution 1 is introduced only immediately before implantation. In this way, it is possible, following a previously conducted antibiogram, to perform an antibiotic coating with the antibiotics that are best suited for the respective micro-organisms.

It is also within the meaning of the invention to introduce solution 2, which contains an amphiphilic component from the groups of the trialkyl ammonium salts, the dialkyl ammonium salts, the dialkyl aryl ammonium salts, the alkylaryl ammonium salts, the diarylammonium salts and the triaryl ammonium salts, into the bodies with interconnecting micro hollow space systems, and after removal of the water to use the bodies treated this way with interconnecting micro hollow space systems as implant materials, into which an aqueous solution of an acid antibiotic which contains carboxyl and/or sulfate groups is introduced only immediately before implantation.

Subsequent examples 1 through 8 serve the purpose of explaining the invention without limiting it.

EXAMPLES

Cuboid, resorbable phosphate glasses with dimensions of 20×20×10 mm were used as bodies with interconnecting pore systems for examples 1 through 8. They had an overall porosity of 65 percent by volume.

The general procedure in the preparation of examples 1 through 5 is as follows:

50 to 100 mg gentamicin sulfate were dissolved in 1 g water (solution 1). Separately, 50 to 200 mg sodium dodecyl sulfate were introduced into 1 g water (solution 2). First the previously prepared aqueous gentamicin sulfate solutions were dripped into the pores of the cuboid phosphate glasses. The sample bodies absorbed the gentamicin sulfate solutions. Afterwards the water in the pores was removed through a drying process with anhydrous calcium chloride. Then the prepared aqueous sodium dodecyl sulfate solutions were dripped into the pores of the dried phosphate glasses. Drying of the sample bodies also took place with anhydrous calcium chloride until mass constancy.

Release of antibiotics of the sample bodies of examples 1 through 5:

The molded bodies produced in examples 1 through 5 were introduced into 20 ml physiological saline solution and stored at 37° C. over a period of 28 days. Samples were taken after 1, 2, 3, 6, 9, 12, 15, 21 and 28 days of storage time. After each sampling, the release medium was replaced completely with a new medium. The antibiotics value determination occurred with an agar diffusion test while employing *Bacillus subtilis* ATCC 6633 as test germ. The results are depicted in Table 2 and clearly show that the coating sample bodies continuously release gentamicin over a period of 28 days. After 28 days the experiment was stopped. The coated molded bodies consequently represent gentamicin deposit forms, which in accordance with the object of the invention release gentamicin to the surrounding aqueous environment over a period of four weeks.

TABLE 2

Results of the microbial determination of the release of gentamicin by the coated sample bodies from examples 1 through 5 depending upon the storage time of the sample bodies in a physiological saline solution at 37° C.

| Ex-ample No. | Release of Gentamicin (cumulative, as gentamicin sulfate AK = 628) [mg] Release Time [d] | | | | | | | | |
|---|---|---|---|---|---|---|---|---|---|
| | 1 | 2 | 3 | 6 | 9 | 12 | 15 | 21 | 28 |
| 1 | 8.8 | 10.5 | 12.1 | 13.8 | 15.2 | 16.4 | 17.5 | 18.6 | 19.4 |
| 2 | 1.2 | 1.5 | 1.8 | 2.1 | 2.4 | 3.0 | 3.8 | 4.7 | 5.5 |
| 3 | 1.2 | 1.4 | 1.6 | 1.8 | 2.0 | 2.2 | 2.5 | 2.7 | 3.1 |
| 4 | 27.5 | 30.4 | 32.8 | 35.3 | 36.8 | 38.2 | 39.2 | 40.4 | 41.4 |
| 5 | 3.0 | 3.2 | 3.6 | 3.8 | 4.0 | 4.2 | 5.0 | 5.3 | 5.7 |

General procedure in the preparation of examples 6 through 8:

The procedure is equivalent to the preparation followed for examples 1 through 5. The only difference is that in this case the solutions 2 were heated to 80 to 90° C. before dripping onto the sample bodies. The examination of the release of gentamicin was performed the same way as that in examples 1 through 5.

TABLE 1

Compositions of solution 1 and solution 2 as well as weights of the uncoated and coated sample bodies of examples 1 through 5.

| Example No. | Composition of Solution 1 | Composition of Solution 2 | Mass of Sample Bodies before Coating [mg] | Mass of Sample Bodies after Coating [mg] | Mass of Coating [mg] |
|---|---|---|---|---|---|
| 1 | 50 mg GS 1000 mg H$_2$O | 50 mg SDS 1000 mg H$_2$O | 3643 | 3734 | 91 |
| 2 | 50 mg GS 1000 mg H$_2$O | 100 mg SDS 1000 mg H$_2$O | 4186 | 4323 | 137 |
| 3 | 50 mg GS 1000 mg H$_2$O | 150 mg SDS 1000 mg H$_2$O | 3244 | 3430 | 186 |
| 4 | 100 mg GS 1000 mg H$_2$O | 100 mg SDS 1000 mg H$_2$O | 3384 | 3581 | 197 |
| 5 | 100 mg GS 1000 mg H$_2$O | 200 mg SDS 1000 mg H$_2$O | 3335 | 3615 | 280 |

GS: gentamicin sulfate (AK = 628)
SDS: sodium dodecyl sulfate

TABLE 3

Compositions of solution 1 and solution 2 as well as weights of the uncoated and coated sample bodies of examples 6 through 8.

| Example No. | Composition of Solution 1 | Composition of Solution 2 | Mass of Sample Bodies before Coating [mg] | Mass of Sample Bodies after Coating [mg] | Mass of Coating [mg] |
|---|---|---|---|---|---|
| 6 | 50 mg GS<br>1000 mg H$_2$O | 50 mg SDS<br>1000 mg H$_2$O | 3945 | 4041 | 96 |
| 7 | 100 mg GS<br>1000 mg H$_2$O | 100 mg SDS<br>1000 mg H$_2$O | 4249 | 4447 | 198 |
| 8 | 50 mg GS<br>1000 mg H$_2$O | 150 mg SDS<br>1000 mg H$_2$O | 3378 | 3575 | 197 |

GS: gentamicin sulfate (AK = 628)
SDS: sodium dodecyl sulfate

Release of antibiotics of the sample bodies of examples 6 through 8:

The release of antibiotics was performed the same way as in examples 1 through 5, and the gentamicin value determination occurred in an equivalent fashion microbially with *Bacillus subtilis* ATCC 6633 as test germ. The results of the release examination are depicted in Table 4. These results show that the sample bodies coated with aqueous gentamicin sulfate solution and with aqueous sodium dodecyl sulfonate solution likewise exhibited a delayed release of gentamicin over a period of 28 days. After 28 days the release attempts were stopped. A comparison of the mass of the gentamicin sulfate used for the antibiotic coating to the mass of the release gentamicin shows that a considerable portion of the gentamicin is still located in the coating after 28 days. The example no. 8 clearly shows that with an increased portion of dodecyl sulfonate in the coating, the release of gentamicin within the first day can be lowered considerably.

TABLE 4

Results of the microbial determination of the release of gentamicin by the coated sample bodies from examples 6 through 8 depending upon the storage time of the sample bodies in a physiological saline solution at 37° C.

| Example No. | Release of Gentamicin (cumulative, as gentamicin sulfate AK = 628) [mg] Release Time [d] | | | | | | | | |
|---|---|---|---|---|---|---|---|---|---|
| | 1 | 2 | 3 | 6 | 9 | 12 | 15 | 21 | 28 |
| 6 | 16.9 | 20.8 | 23.4 | 24.9 | 26.4 | 27.6 | 28.2 | 29.5 | 31.0 |
| 7 | 19.1 | 24.4 | 29.5 | 33.7 | 35.8 | 37.9 | 39.9 | 42.1 | 43.5 |
| 8 | 2.7 | 4.4 | 5.2 | 5.7 | 6.2 | 6.6 | 7.0 | 7.6 | 8.2 |

What is claimed is:

1. Method for the antibiotic coating of bodies with interconnecting microcavities, said method comprising the following steps:
   a) introducing into the microcavities an aqueous solution 1, which comprises at least one easily water-soluble antibiotic component selected from the group consisting of the aminoglycoside antibiotics, the tetracycline antibiotics, the lincosamide antibiotics, the 4-quinolone antibiotics and the chlorhexidines, and an aqueous solution 2, which comprises at least one easily water-soluble amphiphilic component selected from the group consisting of the alkyl sulfates, alkyl sulfonates, alkylaryl sulfates, dialkylaryl sulfates, alkylaryl sulfonates, dialkylaryl sulfonates, cycloalkyl sulfates, cycloalkyl sulfonates, and alkylcycloalkyl sulfates,
   b) removing water between the introduction of solutions 1 and 2, and
   c) forming a coating from components of solutions 1 and 2 in the microcavities, which consists of a sparingly water-soluble deposit.

2. Method according to claim 1, wherein the aqueous solution 1 is introduced into the microcavities first and aqueous solution 2 is subsequently introduced upon removal of the water.

3. Method according to claim 1, wherein the aqueous solution 2 is introduced into the microcavities first and aqueous solution 1 is subsequently introduced upon removal of the water.

4. Method according to claim 1, wherein solution 1 comprises at least one antibiotic substance selected from the group consisting of: allomycin, amicetin, amikacin, apramycin, bekanamycin, betamicin, butirosin, destomycin, dibekacin, dihydrostreptomycin, flambamycin, fortimycin A, fortimycin B, framycetin, gentamicin, hikizimycin, homomycin, hybrimicin, hygromycin B, kasuhamycin, lividomycin, minosamino[m]ycin, neomycin, netimicin, paromomycin, parvulomycin, puromycin A, ribostamycin, rimocidin, ristosamine, ristomycin, sagamycin, sisomicin, sorbistin, specinomycin, streptomycin, tobramycin, tunicamycin, verdamycin, clindamycin and lincomycin, tetracyline, chlortetracycline, oxytetracycline, dimethylchlortetracycline, methacycline, doxycycline, rolitetracycline, minocycline, ciproflaxin, enfloxacin, moxifloxacin, chlorhexidine-di-hydrochloride, chlorhexidine-diacetate and chlorhexidine-di-gluconate.

5. Method according to claim 1, wherein the easily water-soluble antibiotic component is contained in the aqueous solution 1 from 0.1 to 60 percent by mass.

6. Method according to claim 1, wherein the water-soluble amphiphilic component is contained in the aqueous solution 2 from 0.1 to 60 percent by mass.

7. Method according to claim 1, wherein the ratio of the substance quantity of the easily water-soluble antibiotic component of the aqueous solution 1 to the substance quantity of the water-soluble amphiphilic component in the aqueous solution 2 is from 1:1 to 6:1.

8. Method according to claim 1, wherein the antibiotic component in the aqueous solution 1 is in the form of a protonized salt.

9. Method according to claim 8, wherein chloride ions, bromide ions, hydrogen sulfate ions, sulfate ions, dihydrogen phosphate ions, hydrogen phosphate ions, phosphate ions, acetate ions, succinate ions and lactate ions are used as counter-ions.

10. Method according to claim 1, wherein the solutions 1 and/or 2 are introduced into the microcavities through dipping, spraying or dripping.

11. Method according to claim 1, wherein an introduction of an aqueous solution of gentamicin sulfate into the microcavities occurs through dipping or spraying or dripping, a subsequent drying process for removal of the water from the microcavities and a subsequent introduction of an aqueous solution of sodium dodecyl sulfate and/or an aqueous solution of sodium dodecyl sulfonate through dipping or spraying or dripping take place; or in that an introduction of an aqueous solution of ciprofloxacin hydrochloride into the microcavities occurs through dipping or spraying or dripping, a subsequent drying process for removal of the water from the microcavities and a subsequent introduction of an aqueous solution of sodium dodecyl benzyl sulfonate through dipping or spraying or drying take place; or in that an introduction of an aqueous solution of tetracycline hydrochloride and/or chlortetracycline hydrochloride and/or minocycline hydrochloride and/or doxycycline hydrochloride into the microcavities occurs through dipping or spraying or dripping, a subsequent drying process for removal of water from the microcavities and a subsequent introduction of an aqueous solution of sodium dodecyl sulfate and/or an aqueous solution of sodium dodecyl sulfonate taking place through dipping or spraying.

12. Method according to claim 1, wherein upon introduction of the first aqueous solution into the microcavities, the water is removed partially or completely through drying at normal pressure or in a vacuum at temperatures of $-200°$ C. to $1200°$ C.

13. Method according to claim 1, wherein the bodies are molded bodies, and upon formation of the slightly water-soluble deposits, the molded bodies are dried at normal pressure or in a vacuum at temperatures of $-200C$ to $1200C$.

14. Method according to claim 1, wherein the water-soluble amphiphilic component of the aqueous solution 2 comprises at least one substance selected from the group consisting of: sodium dodecyl sulfate, sodium dodecyl sulfonate, sodium tetradecyl sulfate, sodium tetradodecyl sulfonate, sodium hexadecyl sulfate, sodium hexadecyl sulfonate, sodium octadecyl sulfate, sodium octadecyl sulfonate and sodium dodecyl benzyl sulfonate.

15. Method according to claim 1, wherein the microcavities are pores.

16. Method according to claim 1, wherein the body with interconnecting microcavities consists of hydroxyl apatite, tricalcium phosphate, calcium carbonate, calcium sulfate, resorbable glass and resorbable glass ceramics.

17. Method according to claim 1, wherein the bodies with interconnecting microcavities consist of polymers, which are based on L-lactic acid and/or D-lactic acid and/or glycolic acid and/or 2-hydroxyethyl-oxy acetic acid.

18. Method according to claim 17, wherein the bodies with interconnecting microcavities are porous bodies, and are in the form of sponges, foam bodies, shaped masses, felt, fabrics or knits.

19. Method according to claim 1, wherein the bodies consist of titanium, titanium alloys or stainless steel.

20. Method according to claim 1, wherein the antibiotic coating does not completely fill in the volume of the interconnecting microcavities.

21. Method according to claim 1, wherein methanol, ethanol, isopropanol, N,N-dimethyl formamide and/or dimethyl sulfoxide are added as co-solvents to aqueous solution 1 and/or to aqueous solution 2.

22. Method according to claim 1, wherein the antibiotically coated bodies with interconnecting microcavities are used as implants.

23. Method according to claim 1, wherein solution 2 is introduced into the bodies with interconnecting microcavities and that upon removal of the water the bodies treated this way, comprising interconnecting micro hollow space systems, are used as implant material, and solution 1 is not introduced to the implant material until immediately before implantation.

24. A method for the antibiotic coating of bodies with interconnecting microcavities, said method comprising the following steps:
  a) introducing into the microcavities an aqueous solution 1, which comprises at least one easily water-soluble antibiotic component selected from the group consisting of the aminoglycoside antibiotics, the tetracycline antibiotics, the lincosamide antibiotics, the 4-quinolone antibiotics and the chlorhexidines, and an aqueous solution 2, which comprises at least one easily water-soluble amphiphilic component selected from the group consisting of the alkyl sulfates, alkyl sulfonates, alkylaryl sulfates, dialkylaryl sulfates, alkylaryl sulfonates, dialkylaryl sulfonates, cycloalkyl sulfates, cycloalkyl sulfonates, and alkylcycloalkyl sulfates;
  b) removing water between the introduction of solutions 1 and 2; and
  c) forming a coating from components of solutions 1 and 2 in the microcavities, which coating comprises a sparingly water-soluble salt or complex.

* * * * *